United States Patent [19]

Vary

[11] Patent Number: 5,037,757
[45] Date of Patent: Aug. 6, 1991

[54] **PLASMIDLESS STRAIN OF *BACILLUS MEGATERIUM* QM B1551**

[75] Inventor: Patricia S. Vary, Wheaton, Ill.

[73] Assignee: Board of Regents for Northern Illinois University, De Kalb, Ill.

[21] Appl. No.: 75,346

[22] Filed: Jul. 20, 1987

[51] Int. Cl.$^5$ .................... C12N 1/20; C12N 15/00
[52] U.S. Cl. ..................... 435/252.31; 435/252.5; 435/172.3
[58] Field of Search ............ 435/68, 91, 172.1, 172.3, 435/252.3, 252.31–252.35, 320, 837, 69.1, 71.2; 935/72–75

[56] References Cited

U.S. PATENT DOCUMENTS 4,190,495  2/1980  Curtiss, III ..................... 935/73

OTHER PUBLICATIONS

Stahl et al; Chem. Abstr. 99: 100158v (1983).
Vary, P. S., Garbe, J. C., Franzen, M. A. and Frampton, E. W. 1982, MP13, A Generalized Transducing Bacteriophage for *Bacillus megaterium*, J. Bacteriol. 149:1112–1119.
Garbe, J. C. and Vary, P. S. 1981, Bacteriophage MP13 Transduction of *Bacillus megaterium* QM B1551, pp. 83–87, In: *Sporulation and Germination*, H. S. Levinson, A. L. Sonenshein and D. J. Tripper (eds.), American Society for Microbiology, Washington, D.C.
Callahan, J. P., Crawford, I. P., Hess, G. F. and Vary, P. S. 1983, Cotransductional Mapping of the trp-his Region of *Bacillus megaterium*, J. Bacteriol. 154:1455–1458.
Garbe, J. C., Hess, G. F., Franzen, M. A. and Vary, P. S. 1984, Genetics of Leucine Biosynthesis in *Bacillus megaterium*, J. Bacteriol. 157:454–459).
Brown, B. J. and Carlton, B. C. 1980, Plasmid Mediated Transformation in *Bacillus megaterium*, J. Bacteriol. 142:508–512.
Vorobjeva, I. P., Khmel, I. A. and Alfoldi, L. 1980, Transformation of *Bacillus megaterium* Protoplasts by Plasmid DNA, FEMS Microbiology Letters, 7:261–263.
Kieselburg, M. K., Weikert, M. and Vary, P. S. Analysis of Resident and Transformant Plasmids in *Bacillus megaterium*, Bio/Technology, 2:254–259.
Bohall, N. A. and Vary, P. S. Transposition of Tn917 in *Bacillus megaterium*, J. Bacteriol. 167:716–718.
Von Tersch, M. A. and Carlton, B. C. 1984, Molecular Cloning of Structural and Immunity Genes for Megacins A–216 and A–19213 in *B. megaterium*, J. Bacteriol. 160:854–859.
Weiland, Katherine Lee, M. S. Thesis, Department of Biological Sciences, Northern Illinois University, Plasmid Analysis of Megacin Negative Strains of *Bacillus megaterium* QM B1551.

*Primary Examiner*—James Martinell
*Attorney, Agent, or Firm*—Grace J. Fishel

[57] ABSTRACT

A plasmidless mutant strain of *Bacillus megaterium* QM B1551 designataed PV361 is provided which has lost its ability to produce extracellular megacin but otherwise has substantially all of the characteristics of the parent stock.

*B. megaterium* PV361 has been deposited at the NRRL on July 17, 1987 and been given NRRL accession No. B-18241.

2 Claims, 1 Drawing Sheet

PLASMIDLESS STRAIN OF *BACILLUS MEGATERIUM* QM B1551

The invention described herein was made partly in the course of work under a grant(s) or award(s) from the National Science Foundation.

BACKGROUND OF THE INVENTION

1. Field of the Invention

The present invention relates to a plasmidless strain of *Bacillus megaterium* QM B1551 for use as a bacterial cloning host for recombinant plasmids.

*B. megaterium* has been the object of study in many laboratories both for its interesting biochemical reactions, and because it germinates synchronously and sporulates more efficiently than most other Bacillus species. Industrially, *B. megaterium* has been used to produce L-glutamate, pyruvate, cobalamin, single cell protein, and to modify steroids and antibiotics. Up until the present time, however, *B. megaterium* has not been used as a cloning host to any great extent, a function for which another member of the Bacillus species, *Bacillus subtilis*, and *Escherichia coli* have been widely used.

As a cloning host, *E. coli* has a number of shortcomings which are not common to *B. megaterium*. For example, *E. coli* do not secrete proteins in any great quantity and the outer membrane includes an endotoxin. A genetically engineered clone of *E. coli* must therefore be lysed to recover a protein of interest which is often then contaminated with endotoxin. *B. megaterium*, on the other hand, is an efficient secretor of protein and has no endotoxins in the cell wall, making it more suitable for mass production of pharmaceuticals. While "safe" strains of *E. coli* have been developed, "wild" *E. coli* is a human pathogen whereas *B. megaterium* like *B. subtilis* is not.

*B. subtilis* secretes proteins readily but has two different types of extracellular proteases which digest most foreign protein expressed by the cell, greatly decreasing the yield of the protein of interest. Insofar as known, aall protease negative mutants of *B. subtilis* are leaky while *B. megaterium* has only one extracellular protease and some strains are protease negative.

Even though *B. megaterium* has a number of advantages over *E. coli* and *B. subtilis*, it has a number of disadvantages which have stood in the way of its use as a cloning host. Firstly, it is not as well characterized genetically and, secondly, it contains a large number of naturally-occurring plasmids which potentially might interfere with the expression or further genetic manipulation of any foreign plasmid DNA.

2. Brief Description of the Prior Art

In the past few years, our laboratory has made considerable progress in understanding *B. megaterium* QM B1551 genetically. We have isolated and characterized a generalized transducing phage for this species, which has been used almost exclusively for mapping in QM B1551, and have mapped in detail several loci. (Vary, P. S., Garbe, J. C., Franzen, M. A. and Frampton, E. W. 1982. MP13, A generalized transducing bacteriophage for *Bacillus megaterium*. J. Bacteriol. 149:1112-1119; Garbe, J. C. and Vary, P. S. 1981. Bacteriophage MP13 transduction of *Bacillus megaterium* QM B1551, p. 83 -87. In: *Sporulation and Germination*. H. S. Levinson, A. L. Sonenshein and D. J. Tripper (eds.), American Society for Microbiology, Washington, D. C.; Callahan, J. P., Crawford, I. P., Hess, G. F. and Vary, P. S. 1983. Cotransductional mapping of the trp-his region of *Bacillus megaterium*. J. Bacteriol. 154:1112-1116 and Garbe, J. C., Hess, G. F., Franzen, M. A. and Vary, P. S. 1984. Genetics of leucine biosynthesis in *Bacillus megaterium*. J. Bacteriol. 157:454-459).

In 1980 other laboratories reported protoplast transformation in *B. megaterium* 216 with a few naturally-occurring plasmids from Bacillus and Staphylococcus. (Brown, B. J. and Carlton, B. C. 1980. Plasmid mediated transformation in *Bacillus megaterium*. J. Bacteriol. 142:508-512 and Vorobjeva, I. P., Khmel, I. A. and Alfoldi, L. 1980. Transformation of *Bacilus megaterium* protoplasts by plasmid DNA. FEMS Microbiology Letters. 7:261-263). Thereafter, we began to analyze the resident plasmids in *B. megaterium* QM B1551, in which all of the genetic mapping had been done with MP13, and to extend the transformation studies to test the stability of foreign plasmids in QM B1551.

In 1984, we published an article (Kieselburg, M. K., Weikert, M. and Vary, P. S. Analysis of resident and transformant plasmids in *Bacillus megaterium*. Bio/-Technology. 2:254-259) reporting that the resident plasmids of QM B1551 had been analyzed and that several Bacillus cloning plasmids had been successfully transformed into QM B1551 by protoplast fusion. More particularly, we analyzed the plasmid array of *B. megaterium* QM B1551 by sucrose gradient centrifugation, agarose gel electrophoresis and electron microscopy measurements and found seven plasmid sizes ranging in molecular weight from 3.5 to $109 \times 10^6$. The plasmids transformed by protoplast fusion were found to be stable and present in high copy number suggesting that *B. megaterium* QM B1551 might be a desirable cloning host.

Since the use of transposons greatly increases the genetic versatility of an organism, we continued our work with *B. megaterium* QM B1551 by testing whether a transposon could be introduced into QM B1551. In 1986, we reported that transposon Tn917, carried on plasmid pTV1, had been successfully introduced into QM B1551 and transposed efficiently and apparently without hot spots. (Bohall, N. A. and Vary, P. S. Transposition of Tn917 in *Bacillus megaterium*. J. Bacteriol. 167:716-718).

Because at least 11% of the cellular DNA of *B. megaterium* QM B1551 is present as plasmid DNA, it seemed unlikely that QM B1551 had much prospect for use industrially as a cloning host unless it could be cured of its plasmids. Having proved the stability of foreign plasmids in *B. megaterium* QM B1551 and the use of transposons, our attention was now directed to the development of a plasmidless strain.

In earlier work, another laboratory isolated a plasmidless strain of *B. megaterium* 19213, designated VT1600 (ATCC 35985) (Von Tersch, M. A. and Carlton, B. C. 1984. Molecular cloning of structural and immunity genes for megacins A-216 and A-19213 in *B. megaterium*. J. Bacteriol. 160:854-859) but they did not test for expression of recombinant proteins and *B. megaterium* 19213 is much less well characterized genetically than QM B1551.

Our initial attempts to cure *B. megaterium* QM B1551 of its plasmids were only partly successful. In a thesis accepted on June 4, 1985, we reported that sublethal concentrations of novobiocin and ethidium bromide produced a number of strains, some of which were cured of all but a few plasmids, but all of which contained some plasmids. (Katherine Lee Weiland, M. S.

Thesis. Department of Biological Sciences. Northern Illinois University. Plasmid analysis of megacin negative strains of *Bacillus megaterium* QM B1551). Hence, at the time the present invention was made we were doubtful whether a plasmidless strain of QM B1551 could be obtained and, if obtained, whether it would be genetically altered in other ways in view of the large amount of DNA being removed from the cell.

In view of the above, it is an object of the present invention to provide a plasmidles strain of *B. megaterium* QM B1551. It is another object to provide a plasmidless strain of *B. megaterium* QM B1551 in which, like the parent stock, foreign plasmids are stable and transposons can be introduced efficiently and randomly. It is still another object of the present invention to provide a plasmidless strain which retains the parent stock's neutral protease. Other objects and features of the invention will be in part apparent and in part pointed out hereinafter, the scope of the invention being indicated by the subjoined claims.

SUMMARY OF THE INVENTION

A novel plasmidless mutant strain of *B. megaterium* QM B1551 is provided which can be used as a bacterial cloning host for recombinant plasmids. A method for producing the mutant strain and a utility are described.

DETAILED DESCRIPTION OF THE INVENTION

Figure 1:
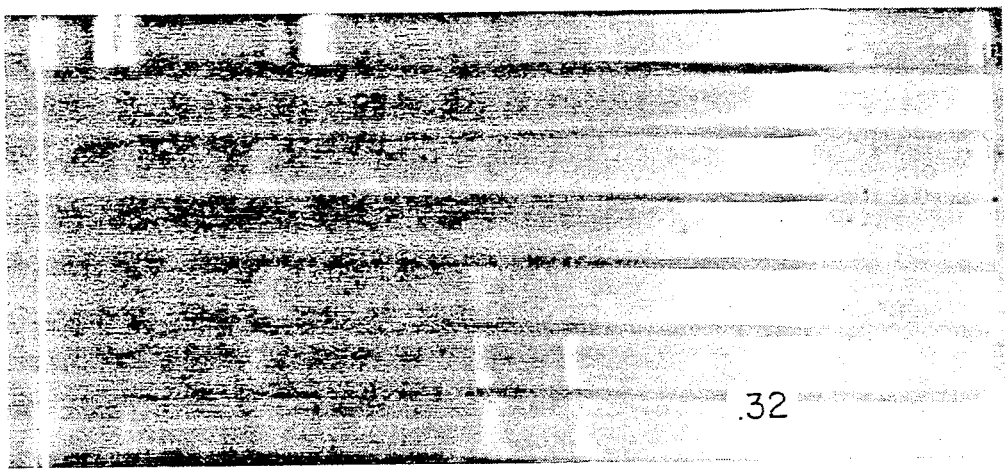
FIG. 1 is a photograph of an agarose gel electrophoresis of a number of strains of *B. megaterium* QM B1551 cured with ethidium bromide under several conditions following storage at −70 degrees C. and subsequent platings on SNB.
Figure 1:

As those skilled in the art will appreciate, producing a plasmid-negative variant of a known organism is an empirical process making use of natural variants as may result by point mutations, phase variations and deletions, in addition to selective or mutagenic effects (or both) which are the result of various physical and/or chemical agents. In advance, it is difficult to predict which condition or combination of conditions will result in a plasmidless strain or, for that matter, that any condition will produce such a strain. The curing of a strain having as many as seven different sizes of plasmids, making up 11% of cellular DNA is particularly speculative. It is also difficult to predict what other genetic changes may occur and to what extent the mutant strain might resemble the parent stock. Typical physical and chemical agents include elevated temperature, thymine starvation, chemical mutagens, ultraviolet light, nickel and cobalt, acridines and other intercalating dyes and so forth. Such a process is called "curing" and may be taken to mean that the plasmid is selectively inactivated or that it is inhibited in replication. For our purpose, we use the term in the more restrictive sense that the plasmid has been inhibited in replication and therefore absent from the daughter cell.

Applying various curing techniques to *B. megaterium* QM B1551, we discovered a plasmidless strain, which we designated PV361, a biologically pure culture of which is available in the Agricultural Research Service Culture Collection at the Agricultural Research Culture Collection (NRRL) International Depositary Authority, 1815 N. University Street, Peoria, Ill. 61604, U.S.A. under NRRL accession No. B-18241. More particularly, strain PV361 was selected from a number of strains produced from a culture of *B. megaterium* QM B1551 grown in supplemented nutrient broth containing per liter 8 g of nutrient broth (Difco Laboratories), 1 g of glucose, 13.4 mM KCl, 0.02 mM $MnCl_2$, 1 uM $FeSO_4$, 1 mM $MgSO_4$ and 1 mM $CaCl_2$. Growth was continued to an absorbance at 660 nm in a 1 cm light path of 6.8–8.0. The culture was diluted to $10^{-3}$ cells/ml in MC broth and 0.1 ml was then added to 0.9 ml of SNB broth containing a concentration of ethidium bromide in an amount from about 5 to about 200 ng/ml as a curing agent. MC broth contained per liter 5 g glucose, 2 g $(NH_4)SO_4$, 14 g $K_2HPO_4$, 6 g $KH_2PO_4$, 1 g trisodium citrate . $2H_2O$, 0.2 g $MgSO_4$ . $7H_2O$, 3.6 uM $FeCl_2$, 0.1 mM $MgCl_2$ and 0.1 mM $CaCl_2$. The concentrations of ethidium bromide used were 0.5, 1.0, 2.0, 10.0, 20.0, 100 and 200 ng/ml. The tubes were then incubated with shaking at an elevated temperature between about 30 and about 50 degrees C. —namely, at 37 and 44 degrees C. for 24 hours. The tubes having the highest concentration of curing agent that allowed growth were diluted and streaked on SNB plates. Single colonies were then picked to master plates, allowed to sporulate and the spores stored on disks and frozen.

Portions from each stored strain were streaked on SNB plates, incubated at 30 degrees overnight and subjected to agarose gel electrophoresis under the same conditions as described for QM B1551 in our above-mentioned article in Bio/Technology to determine the presence and estimated size of any remaining plasmids. Various strains were fornd to have been cured of various of the plasmids.

Agarose gel electrophoresis was in 0.5% agarose with a Tris-phosphate buffer using 13.5 cm × 14 cm × 4 mm gels in a submerged horizontal gel apparatus. Sample buffer was 25% sucrose, 5 mM sodium acetate, 0.05% bromphenol blue and 0.1% SDS. The samples were run into the gel for 30 minutes at 25 volts before increasing to 150 volts for 3–4 hours. Gels were stained in the dark in electrophoresis buffer containing 1 ug/ml ethidium bromide and were viewed on a LJ5-6Tl-F500 long wave transilluminator (La Jolla, Calif.). Photography was with Polaroid type 55 P/N film through a Wratten 23A gelatin filter (Kodak).

One strain in particular, which was designated PV200, and derived from QM B1551 treated with ethidium bromide at a concentration of 1.0 ng and at a temperature of 44 degrees C. as set forth above was found to have been cured of all but three plasmids—namely, pVY105, pVY113 and pVY132. As shown in FIG. 1, following storage at −70 degrees C. and/or as a result of subsequent platings on SNB, strain PV200 spontaneously lost its remaining plasmids and became the plasmidless strain which we designated PV361.

PV361 grows, sporulates and transforms (using polyethylene glycol fusion of protoplasts) like *B. megaterium* QM B1551 and is useful as a cloning host for recombinant plasmids. Plasmids transformed into PV361 are stable and present in high copy number. Recombinant plasmids that have been successfully introduced into PV361 include pTV1, pTV32 and pTV53 (all plasmids carrying modifications of transposon Tn917); pHV33 (a shuttle plasmid between *E. coli* and *B. subtilis*) and pOCl (a plasmid carrying the lux genes from Vibrio). The plasmids carrying modifications of transposon Tn917 were introduced into PV361 efficiently and Tn917 transposes apparently without hot spots. *B. subtilis* integrative plasmid pJH101 carrying *B.*

*megaterium* ssp genes (small acid soluble spore genes) has also been successfully introduced into PV361 and shown to integrate by the Campbell mechanism as in *B. subtilis*. (Setlow, Sussman and Vary. Manuscript in preparation .) PV361 is sensitive to transducing phage MP13, still further increasing its genetic versatility. It produces a neutral protease, like the parent stock, but advantageously has lost the ability to produce an extracellular megacin. This is desirable for use of PV361 as a cloning host as it eliminates a protein to be separated from a foreign protein of interest which is expressed by the biologically engineered organism. PV361 otherwise has substantially all of the characteristics of QM B1551 from which it was derived.

In view of the above, it will be seen that the several objects of the invention are achieved and other advantageous results attained.

What is claimed is:

1. A plasmidless culture of *Bacillus megaterium* derived from *Bacillus megaterium* QM B1551 which is deposited under NRRL accession No. B-18241 in the Agricultural Research Service Culture Collection suitable for use as a bacterial cloning host for recombinant plasmids.

2. A transformed host cell comprising *Bacillus megaterium* QM B1551 (NRRL B-18241) and further comprising a foreign plasmid.

* * * * *

UNITED STATES PATENT AND TRADEMARK OFFICE
CERTIFICATE OF CORRECTION

PATENT NO. : 5,037,757
DATED : August 6, 1991
INVENTOR(S) : Patricia S. Vary

It is certified that error appears in the above-identified patent and that said Letters Patent is hereby corrected as shown below:

In the drawings, Fig. 1 should be printed darker.

A photocopy of the original drawing as it should appear in the printed copy of the patent is attached.

Signed and Sealed this

Sixteenth Day of February, 1993

Attest:

STEPHEN G. KUNIN

*Attesting Officer*    Acting Commissioner of Patents and Trademarks